United States Patent
Briscoe et al.

(10) Patent No.: US 6,527,890 B1
(45) Date of Patent: Mar. 4, 2003

(54) MULTILAYERED CERAMIC MICRO-GAS CHROMATOGRAPH AND METHOD FOR MAKING THE SAME

(75) Inventors: Cynthia G. Briscoe, Tempe, AZ (US); Huinan Yu, Chandler, AZ (US); Piotr Grodzinski, Chandler, AZ (US); Rong-Fong Huang, Tempe, AZ (US); Jeremy W. Burdon, Scottsdale, AZ (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/460,283

(22) Filed: Dec. 9, 1999

Related U.S. Application Data (63) Continuation-in-part of application No. 09/337,086, filed on Jun. 21, 1999, which is a continuation-in-part of application No. 09/235,081, filed on Jan. 21, 1999.
(60) Provisional application No. 60/103,701, filed on Oct. 9, 1998.

(51) Int. Cl.⁷ .............................. B32B 31/26; B01L 3/00

(52) U.S. Cl. .................................. 156/89.11; 156/89.12; 96/101

(58) Field of Search ........................... 156/89.11, 89.12; 96/101

(56) References Cited

U.S. PATENT DOCUMENTS

| | | | |
|---|---|---|---|
| 3,182,394 A | * | 5/1965 | Jentzsch |
| 3,283,483 A | * | 11/1966 | Halasz et al. |
| 3,293,072 A | | 12/1966 | Doolittle et al. |
| 3,506,473 A | | 4/1970 | Ettre |
| 3,574,029 A | | 4/1971 | Ettre et al. |
| 3,598,679 A | | 8/1971 | Ettre et al. |
| 3,948,706 A | | 4/1976 | Schmeckenbecher |
| 3,956,052 A | | 5/1976 | Koste et al. |
| 3,991,029 A | | 11/1976 | Adelman |
| 4,035,613 A | * | 7/1977 | Sagawa et al. |
| 4,098,645 A | | 7/1978 | Hartdegen et al. |
| 4,118,237 A | | 10/1978 | Beall et al. |
| 4,414,323 A | | 11/1983 | Masuda |
| 4,474,889 A | | 10/1984 | Terry et al. |
| 4,523,121 A | | 6/1985 | Takahashi et al. |

(List continued on next page.)

FOREIGN PATENT DOCUMENTS

| | | | |
|---|---|---|---|
| DE | 2 364 159 | * | 6/1974 |
| DE | 19725948 | | 12/1998 |
| EP | 0 313 090 | * | 4/1989 |

(List continued on next page.)

OTHER PUBLICATIONS

Gongora–Rubio et al., "Overview of low temperature co–fired ceramics tape technology for meso–system technology (MsST)", Sensors and Actuators, 89:222–241 (2001).

Espinoza–Vallejos, P. et al., "MESO (Intermediate)–Scale electromechanical systems for the measurement and control of sagging in LTCC structures," Med. Res. Soc. Symp. Pros. 518:73–79 (1998).

(List continued on next page.)

*Primary Examiner*—Curtis Mayes
(74) *Attorney, Agent, or Firm*—Douglas W. Gilmore (57) ABSTRACT

A micro-gas chromatograph column is formed by texturing a channel into a plurality of green-sheet layers, which are then sintered together to form a substantially monolithic structure. A thick-film paste may be added to the channel textured in the green-sheet layers to provide a porous plug sintered in the micro-gas chromatograph column in the substantially monolithic. A thermal conductivity detector is formed in the substantially monolithic structure by depositing a conductive thick-film paste on the surface of one of the green-sheet layers to define a resistor in an exit channel of the micro-gas chromatograph column.

7 Claims, 2 Drawing Sheets

U.S. PATENT DOCUMENTS

| | | |
|---|---|---|
| 4,551,357 A | 11/1985 | Takeuchi |
| 4,610,741 A | 9/1986 | Mase et al. |
| 4,737,208 A | 4/1988 | Bloechle et al. |
| 4,793,920 A * | 12/1988 | Cortes et al. |
| 4,806,295 A | 2/1989 | Trickett et al. |
| 4,833,000 A | 5/1989 | Trickett et al. |
| 4,840,893 A | 6/1989 | Hill et al. |
| 4,929,295 A | 5/1990 | Kohno et al. |
| 4,935,040 A | 6/1990 | Goedert |
| 4,939,021 A | 7/1990 | Aoki et al. |
| 4,985,098 A | 1/1991 | Kohno et al. |
| 4,991,283 A | 2/1991 | Johnson et al. |
| 5,008,151 A | 4/1991 | Tominaga et al. |
| 5,089,071 A | 2/1992 | Tominaga et al. |
| 5,164,319 A | 11/1992 | Hafeman et al. |
| 5,174,842 A | 12/1992 | Hamuro et al. |
| 5,176,771 A | 1/1993 | Bravo et al. |
| 5,187,096 A | 2/1993 | Giaever et al. |
| 5,194,133 A | 3/1993 | Clark et al. |
| 5,254,191 A | 10/1993 | Mikeska et al. |
| 5,261,986 A | 11/1993 | Kawabata et al. |
| 5,265,327 A | 11/1993 | Faris et al. |
| 5,271,150 A | 12/1993 | Inasaka |
| 5,312,527 A | 5/1994 | Mikkelsen et al. |
| 5,312,674 A | 5/1994 | Haertling et al. |
| 5,340,543 A * | 8/1994 | Annino et al. |
| 5,358,593 A | 10/1994 | Hamuro et al. |
| 5,412,499 A | 5/1995 | Chiu et al. |
| 5,435,875 A | 7/1995 | Saitoh et al. |
| 5,478,420 A | 12/1995 | Gauci et al. |
| 5,532,128 A | 7/1996 | Eggers et al. |
| 5,534,092 A | 7/1996 | Ogawa et al. |
| 5,534,328 A | 7/1996 | Ashmead et al. |
| 5,538,582 A | 7/1996 | Natarajan et al. |
| 5,540,884 A | 7/1996 | Chiao |
| 5,552,270 A | 9/1996 | Khrapko et al. |
| 5,565,729 A | 10/1996 | Faris et al. |
| 5,583,281 A | 12/1996 | Yu |
| 5,587,128 A * | 12/1996 | Wilding et al. |
| 5,589,136 A | 12/1996 | Northrup et al. |
| 5,591,578 A | 1/1997 | Meade et al. |
| 5,595,712 A | 1/1997 | Harbster et al. |
| 5,601,673 A | 2/1997 | Alexander |
| 5,607,535 A | 3/1997 | Tsukada et al. |
| 5,611,214 A | 3/1997 | Wegeng et al. |
| 5,614,053 A | 3/1997 | Toudo et al. |
| 5,639,508 A | 6/1997 | Okawa et al. |
| 5,653,939 A | 8/1997 | Hollis et al. |
| 5,670,322 A | 9/1997 | Eggers et al. |
| 5,676,788 A | 10/1997 | Natarajan et al. |
| 5,681,410 A | 10/1997 | Takeuchi et al. |
| 5,683,535 A | 11/1997 | Karr |
| 5,707,476 A | 1/1998 | Bezama et al. |
| 5,728,244 A | 3/1998 | Nanataki et al. |
| 5,746,874 A | 5/1998 | Natarajan et al. |
| 5,753,060 A | 5/1998 | Mori |
| 5,759,320 A | 6/1998 | Natarajan et al. |
| 5,779,833 A | 7/1998 | Cawley et al. |
| 5,785,800 A | 7/1998 | Natarajan et al. |
| 5,792,379 A | 8/1998 | Dai et al. |
| 5,795,422 A * | 8/1998 | Chatterjee et al. |
| 5,795,545 A | 8/1998 | Koripella et al. |
| 5,811,062 A | 9/1998 | Wegeng et al. |
| 5,821,181 A | 10/1998 | Bethke et al. |
| 5,855,803 A | 1/1999 | Bailey et al. |
| 5,858,195 A | 1/1999 | Ramsey |
| 5,860,202 A | 1/1999 | Okawa et al. |
| 5,939,312 A | 8/1999 | Baier et al. |
| 5,961,930 A | 10/1999 | Chatterjee et al. |
| 5,961,932 A | 10/1999 | Ghosh et al. |
| 5,965,092 A | 10/1999 | Chatterjee et al. |
| 5,976,472 A | 11/1999 | Chatterjee et al. |
| 5,993,750 A | 11/1999 | Ghosh et al. |
| 6,190,559 B1 * | 2/2001 | Valaskovic ................ 96/101 X |

FOREIGN PATENT DOCUMENTS

| | | |
|---|---|---|
| EP | 0649008 B1 | 6/1998 |
| EP | 0 870 541 A2 | 10/1998 |
| EP | 0744389 B1 | 3/1999 |
| JP | 53-49264 | 5/1978 |
| JP | 62-288154 | * 12/1986 |
| JP | 63-42147 | 2/1988 |
| JP | 63-239999 | 10/1988 |
| JP | 2-117117 | 5/1990 |
| JP | 2-166793 | 6/1990 |
| JP | 2-219603 | 9/1990 |
| JP | 3-148196 | 6/1991 |
| JP | 4-114961 | 4/1992 |
| JP | 5-267844 | 10/1993 |
| JP | 6-104572 | 4/1994 |
| JP | 6-152135 | 5/1994 |
| JP | 6-290987 | 10/1994 |
| JP | 7-289886 | * 11/1995 |
| JP | 8-108422 | 4/1996 |
| JP | 8-267421 | 10/1996 |
| WO | 98/50154 A1 | 11/1998 |
| WO | WO 99/23324 A1 | 5/1999 |
| WO | WO 00/21659 A1 | 4/2000 |
| WO | WO 01/35484 A1 * | 5/2001 |
| WO | WO 01/41931 A2 | 6/2001 |

OTHER PUBLICATIONS

Gongora–Rubio, M. et al., "A simple thermistor based flow sensor using the LTCC–ML technology" Quimica Analitica, 18:30–32 (1999).

Gongora–Rubio, M. et al., "A Meso–scale Electro–magetically actuated normally closed valve realized on LTCC tapes" Part of the SPIE Conference on Microfluidic Devices and Systems, II, Sep. 1999, SPIE 3877: 230–239.

Gongora–Rubio, M. et al., "The utilization of low temperature cofired ceramics (LTTC–ML), technology for meso–scale EMS, a simple thermistor based flow sensor" Sensors and Actuators, 73:215–221 (1999).

Gui, Z. et al., "Influence of additives on sintering processing and properties of high performance piezoelectric ceramics" Solid State Phenomina. vol. 25&26: 309–316 (1992).

Kim, M. et al., "The fabrication of flow conduits in ceramic tapes and the measurement of fluid flow through these conduits" DSC–vol. 66. Micro–Electro–Mechanical Systems (MEMS) 171–177 (1998).

Liu, J.H. et al., "Study of thick–film pH sensors" Sensors and Actuatoors, vol. 13–14: 566–567 (1993).

Mistler, R. "Tape casting: The basic process for meeting the needs of the Electronics Industry" Ceramic Bulletin, 69(6): 1022–1026 (1990).

Provamce, J.D. "Performance review of thick film materials" reprinted from Insulation Circuits (Apr. 1977).

Santiago–Aviles, J.J. et al., "The utilization of low temperature co–fired ceramic tapes for 3 dimensional meso–scale fabrication" Quimica Analitica, 18(suppl.1): 33–34 (1999).

Vogelstein et al., "Preparative and analytical purification of DNA from agarose," 1979, Proc. Natl. Acad. Sci. 76:615.

Stephen C. Terry, John H. Jerman and James B. Angell, "A Gas Chromatographic Air Analyzer Fabricated on a Silicon Wafer", IEEE Transactions on Electron Devices, v. ED–26, No. 12, p. 1880–86 (Dec. 1979).

Rocky R. Reston, Edward S. Kolesar, Jr., "Silicon–Micromachined Gas Chromatography System Used to Separate and Detect Ammonia and Nitrogen Dioxide—Part I: Design, Fabrication, and Integration of the Gas Chromatography System", J. Microeletromechanical Systems, 3, No. 4, p. 134–46 (Dec. 1994).

Conrad M. Yu, Matthew Lucas, Jackson C. Koo, Paul Stratton, Terri DeLima, Elaine Behymer, "A High Performance Hand—Held Gas Chromatograph", Micro–Electro Mechanical Systems, v. 66, p. 481–86 (Apr. 28, 1998).

Goib Wiranto, Noel D. Samaan, Dennis E. Mulcahy, David E. Davey, "Microfabrication of Capillary Columns on Silicon", Proceedings of SPIE, v. 3242, p. 59–64 (Dec. 1997).

Marc Madou, "Fundamentals of Microfabrication", p. 498–502 (1979).

* cited by examiner-

MULTILAYERED CERAMIC MICRO-GAS CHROMATOGRAPH AND METHOD FOR MAKING THE SAME

CROSS-REFERENCE TO RELATED APPLICATIONS

This application is a continuation-in-part of U.S. application Ser. No. 09/337,086, filed on Jun. 21, 1999, which is a continuation-in-part of U.S. application Ser. No. 09/235,081, filed on Jan. 21, 1999, which, in turn, claims the benefit of U.S. Provisional Application No. 60/103,701, filed Oct. 9, 1998. The disclosure of U.S. application Ser. No. 09/337,086 is fully incorporated herein by reference.

BACKGROUND OF THE INVENTION

1. Field of the Invention

This invention relates to the field of gas chromatography. More particularly, this invention relates to a micro-gas chromatograph device that is formed from multiple layers of green-sheet and also relates to methods for making such devices.

2. Description of Related Art

Gas chromatography is a well-established analytical technique that is commonly used for the separation and detection of the various chemical components present in gases and low boiling point liquids. The technique is widely used in organic chemistry research, pharmaceutical development, and forensic specimen analysis. A gas chromatography system typically has five major components: (1) a carrier gas; (2) a sample injector; (3) a gas chromatography column; (4) a detector; and (5) a data processing system. The carrier gas, also referred to as the mobile phase, is a high-purity and relatively inert gas, such as helium. The carrier gas flows through the column throughout the separation process. The sample injector introduces a precise and, typically, very small volume of the sample, in gaseous form, into the flow of carrier gas into the column. The gaseous sample typically includes a number of different chemical components that are intended to be separated by the gas chromatograph. To effect this separation, the inside of the column is coated with a stationary phase that adsorbs the different chemical components in the sample to differing degrees. These differences in adsorption cause differing propagation delays for the chemical components as they travel down the column, thereby effecting a physical separation of the sample into its chemical components. The detector is located after the column and serves to detect the various chemical components in the sample as they emerge from the column at different times. The data processing system reads the detector and is typically able to store, process, and record the results.

Conventional gas chromatography systems are bench top instruments that are designed for use in a laboratory setting. However, in many instances, it is desirable to have a portable gas chromatograph that can be used outside of the laboratory, such as where the samples are collected. Portable gas chromatographs have potential application for leak detection, environmental screening, monitoring the volatile organic chemical content of waste water, and in the detection and analysis of vent gases, land fill gases, and natural gas.

One of the most significant barriers to making a portable gas chromatograph device is that the separation efficiency of the device is directly proportional to the length of the column. Currently, a few portable gas chromatography systems are available, but they are only suited for the detection of certain specific substances. In recent years, efforts have been made to fabricate the column and detector using newly developed micromachining techniques in order to provide miniaturized gas chromatography systems that are portable and that can analyze multiple substances.

Such micro-gas chromatograph devices are most commonly fabricated from silicon substrates. However, such substrates have a number of disadvantages. For example, a micro-gas chromatograph column has been fabricated by etching an interlocking spiral channel about 10 microns deep and 300 microns wide in a silicon wafer. See Reston, et al., "Silicon-Micromachined Gas Chromatography System Used to Separate and Detect Ammonia and Nitrogen Dioxide," *J. Microelectromechanical Systems,* 3:134–146 (1994). The top surface of the column was defined by a borosilicate glass plate anodically bonded to the silicon wafer. Because the bond frequently failed along the edges, presumably because of the mismatch in thermal expansion coefficients of the two materials, the column was restricted to an area in the center of the wafer about 3.8 cm in diameter. Accordingly, the anodic bonding process used with silicon substrates serves to limit the length and, thus, the separation efficiency of the column. Another limitation on the length of the column in the Reston device is that it lies all in one plane, namely, the interface of the silicon and glass layers. Still another disadvantage with this approach is that, because the column is defined by dissimilar materials, thermal gradients can develop that further decrease the column's separation efficiency.

Goedert, U.S. Pat. No. 4,935,040 discloses a micro-gas chromatograph device that is made up of multiple layers. Several planar column sections are defined by the interfaces between pairs of layers, and the planar column sections are connected in series to increase the available column length. The layers alternate between silicon and glass wafers that are joined together by anodic bonding. Alternatively, the layers may be silicon, with bonding effected by a thin layer of silica between. By using multiple layers, the Goedert device is able to provide a longer column. However, anodically bonding multiple layers is difficult to achieve reliably.

SUMMARY OF THE INVENTION

In a first principal aspect, the present invention provides a multilayered micro-gas chromatograph device for analyzing an analyte gas that includes a plurality of chemical components. The multilayered micro-gas chromatograph device comprises a substantially monolithic structure having a micro-gas chromatograph column defined therein. The substantially monolithic structure is formed from a plurality of green-sheet layers sintered together, wherein the green-sheet layers include particles selected from the group consisting of ceramic particles, glass particles, and glass-ceramic particles. The micro-gas chromatograph column has an inlet port for receiving the analyte gas and an outlet port for releasing the analyte gas. A stationary phase for differentially adsorbing chemical components in the analyte gas is disposed in a portion of the micro-gas chromatograph column.

In a second principal aspect, the present invention provides a micro-gas chromatography system comprising a supply of a carrier gas, a sample injection valve, a micro-gas chromatograph column, and a detector. The sample injection valve is connected to the supply and injects a sample gas into the carrier gas to provide an analyte gas. The micro-gas chromatograph column separates the analyte gas into a plurality of chemical components. It has an inlet port and an outlet port, with the inlet port connected to the sample injection valve to receive the analyte gas. The micro-gas chromatography column is defined in a substantially monolithic structure that is formed from a plurality of green-sheet layers sintered together. The green-sheet layers include particles selected from the group consisting of ceramic particles, glass particles, and glass-ceramic particles. The detector is connected to the outlet port and detects the plurality of chemical components separated by the micro-gas chromatograph column.

In a third principal aspect, the present invention provides a method for making a multilayered micro-gas chromatograph device. A plurality of green-sheet layers are textured in a predetermined pattern to define a micro-gas chromatograph column. The green-sheet layers include particles selected from the group consisting of ceramic particles, glass particles, and glass-ceramic particles. A thick-film paste is applied to at least a portion of the predetermined pattern in the green-sheet layers. The green-sheet layers are sintered together at a predetermined temperature for a predetermined amount of time to form a substantially monolithic structure having a micro-gas chromatograph column defined therein, with a porous plug, formed from the thick-film paste, disposed in the micro-gas chromatograph column.

DETAILED DESCRIPTION OF THE INVENTION

Figure 1:
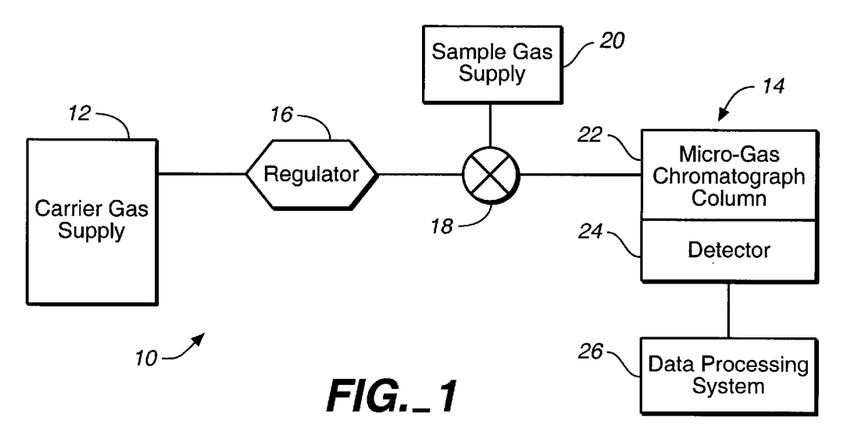
FIG. 1 is a schematic diagram of a micro-gas chromatograph system, in accordance with a preferred embodiment of the present invention.

Shown in FIG. 1 is a micro-gas chromatography system 10, in accordance with a preferred embodiment of the present invention. A carrier gas supply 12 provides a flow of a carrier gas to a micro-gas chromatograph device 14 via a regulator 16 and a sample injection valve 18. Regulator 16 is used to adjust the flow rate of the carrier gas. Sample injection valve 18 injects a small precise volume of sample gas from a sample gas supply 20. Suitable sample injection valves are commercially available, such as model no. NC1500 from Redwood Microsystems, Inc., Menlo Park, Calif.

In accordance with the present invention, micro-gas chromatograph device 14 comprises a multilayered structure described in greater detail hereafter that includes a micro-gas chromatograph column 22. A detector 24 is provided at the output of column 22. Preferably, detector 24 is an integral part of the same multilayered structure that defines column 14. However, detector 24 may also be an external device connected to the output of column 22.

A data processing system 26 reads detector 24, preferably as a function of time, so as to obtain data indicative of the separated chemical components from the sample that pass by detector 24. Data processing system 26 is preferably able to store, record, and process this data, as in conventional. For example, data processing system 26 may be based on LabVIEW data acquisition, control, analysis, and presentation software available from National Instruments Corp., Austin, Tex.

Micro-gas chromatograph device 14, in accordance with the present invention, is made from layers of green-sheet that have been laminated and sintered together to form a substantially monolithic structure. Green-sheet is a composite material that includes inorganic particles of glass, glass-ceramic, ceramic, or mixtures thereof, dispersed in a polymer binder, and may also include additives such as plasticizers and dispersants. The green-sheet is preferably in the form of sheets that are 50 to 250 microns thick. The ceramic particles are typically metal oxides, such as aluminum oxide or zirconium oxide. An example of such a green-sheet that includes glass-ceramic particles is "AX951" that is sold by E.I. Du Pont de Nemours and Company. An example of a green-sheet that includes aluminum oxide particles is "Ferro Alumina" that is sold by Ferro Corp. The composition of the green-sheet may also be custom formulated to meet particular applications. The green-sheet layers are laminated together and then fired to form a substantially monolithic multilayered structure. The manufacturing, processing, and applications of ceramic green-sheets are described generally in Richard E. Mistler, "Tape Casting: The Basic Process for Meeting the Needs of the Electronics Industry," Ceramic Bulletin, vol. 69, no. 6, pp. 1022–26 (1990), and in U.S. Pat. No. 3,991,029, which are incorporated herein by reference.

The method for fabricating micro-gas chromatograph device 14 begins with providing sheets of green-sheet that are preferably 50 to 250 microns thick. The sheets of green-sheet are cut to the desired size, typically 6 inches by 6 inches for conventional processing Each green-sheet layer may then be textured using various techniques to form desired structures, such as vias, channels, or cavities, in the finished multilayered structure.

Various techniques may be used to texture a green-sheet layer. For example, portions of a green-sheet layer may be punched out to form vias or channels. This operation may be accomplished using conventional multilayer ceramic punches, such as the Pacific Trinetics Corp. Model APS-8718 Automated Punch System. Instead of punching out part of the material, features, such as channels and wells may be embossed into the surface of the green-sheet by pressing the green-sheet against an embossing plate that has a negative image of the desired structure. Texturing may also be accomplished by laser tooling with a laser via system, such as the Pacific Trinetics LVS-3012.

Next, a wide variety of materials may be applied, preferably in the form of thick-film pastes, to each textured green-sheet layer. For example, electrically conductive pathways may be provided by depositing metal-containing thick-film pastes onto the green-sheet layers. Thick-film pastes typically include the desired material, which may be either a metal or a dielectric, in the form of a powder dispersed in an organic vehicle, and the pastes are designed to have the viscosity appropriate for the desired deposition technique, such as screen-printing. The organic vehicle may include resins, solvents, surfactants, and flow-control agents. The thick-film paste may also include a small amount of a flux, such as a glass frit, to facilitate sintering. Thick-film technology is further described in J. D. Provance, "Performance Review of Thick Film Materials," *Insulation/Circuits* (April, 1977) and in Morton L. Topfer, *Thick Film Microelectronics,*

*Fabrication, Design, and Applications* (1977), pp. 41–59, which are incorporated herein by reference.

The porosity of the resulting thick-film can be adjusted by adjusting the amount of organic vehicle present in the thick-film paste. Specifically, the porosity of the thick-film can be increased by increased the percentage of organic vehicle in the thick-film paste. Similarly, the porosity of a green-sheet layer can be increased by increasing the proportion of organic binder. Another way of increasing porosity in thick-films and green-sheet layers is to disperse within the organic vehicle, or the organic binder, another organic phase that is not soluble in the organic vehicle. Polymer microspheres can be used advantageously for this purpose.

To add electrically conductive pathways, the thick film pastes typically include metal particles, such as silver, platinum, palladium, gold, copper, tungsten, nickel, tin, or alloys thereof. Silver pastes are preferred. Examples of suitable silver pastes are silver conductor composition numbers 7025 and 7713 sold by E.I. Du Pont de Nemours and Company.

The thick-film pastes are preferably applied to a green-sheet layer by screen-printing. In the screen-printing process, the thick-film paste is forced through a patterned silk screen so as to be deposited onto the green-sheet layer in a corresponding pattern. Typically, the silk screen pattern is created photographically by exposure to a mask. In this way, conductive traces may be applied to a surface of a green-sheet layer. Vias present in the green-sheet layer may also be filled with thick-film pastes. If filled with thick-filled pastes containing electrically conductive materials, the vias can serve to provide electrical connections between layers.

After the desired structures are formed in each layer of green-sheet, preferably a layer of adhesive is applied to either surface of the green-sheet. Preferably, the adhesive is a room-temperature adhesive. Such room-temperature adhesives have glass transition temperatures below room temperature, i.e., below about 20° C., so that they can bind substrates together at room temperature. Moreover, rather than undergoing a chemical change or chemically reacting with or dissolving components of the substrates, such room-temperature adhesives bind substrates together by penetrating into the surfaces of the substrates. Sometimes such room-temperature adhesives are referred to as "pressure-sensitive adhesives." Suitable room-temperature adhesives are typically supplied as water-based emulsions and are available from Rohm and Haas, Inc. and from Air Products, Inc. For example, a material sold by Air Products, Inc. as "Flexcryl 1653" has been found to work well.

The room-temperature adhesive may be applied to the green-sheet by conventional coating techniques. To facilitate coating, it is often desirable to dilute the supplied pressure-sensitive adhesive in water, depending on the coating technique used and on the viscosity and solids loading of the starting material. After coating, the room-temperature adhesive is allowed to dry. The dried thickness of the film of room-temperature adhesive is preferably in the range of 1 to 10 microns, and the thickness should be uniform over the entire surface of the green-sheet. Film thicknesses that exceed 15 microns are undesirable. With such thick films of adhesive voiding or delamination can occur during firing, due to the large quantity of organic material that must be removed. Films that are less than about 0.5 microns thick when dried are too thin because they provide insufficient adhesion between the layers.

From among conventional coating techniques, spin-coating and spraying are the preferred methods. If spin-coating is used, it is preferable to add 1 gram of deionized water for every 10 grams of "Flexcryl 1653." If spraying is used, a higher dilution level is preferred to facilitate ease of spraying. Additionally, when room-temperature adhesive is sprayed on, it is preferable to hold the green-sheet at an elevated temperature, e.g., about 60 to 70° C., so that the material dries nearly instantaneously as it is deposited onto the green-sheet. The instantaneous drying results in a more uniform and homogeneous film of adhesive.

After the room-temperature adhesive has been applied to the green-sheet layers, the layers are stacked together to form a multilayered green-sheet structure. Preferably, the layers are stacked in an alignment die, so as to maintain the desired registration between the structures of each layer. When an alignment die is used, alignment holes must be added to each green-sheet layer.

Typically, the stacking process alone is sufficient to bind the green-sheet layers together when a room-temperature adhesive is used. In other words, little or no pressure is required to bind the layers together. However, in order to effect a more secure binding of the layers, the layers are preferably laminated together after they are stacked.

The lamination process involves the application of pressure to the stacked layers. For example, in the conventional lamination process, a uniaxial pressure of about 1000 to 1500 psi is applied to the stacked green-sheet layers that is then followed by an application of an isostatic pressure of about 3000 to 5000 psi for about 10 to 15 minutes. at an elevated temperature, such as 70° C. Adhesives do not need to be applied to bind the green-sheet layers together when the conventional lamination process is used.

However, pressures less than 2500 psi are preferable in order to achieve good control over the dimensions of Such structures as internal or external cavities and channels. Even lower pressures are more desirable to allow the formation of larger structures, such as cavities and channels. For example, if a lamination pressure of 2500 psi is used, the size of well-formed internal cavities and channels is typically limited to no larger than roughly 20 microns. Accordingly, pressures less than 1000 psi are more preferred, as such pressures generally enable structures having sizes greater than about 100 microns to be formed with some measure of dimensional control. Pressures of less than 300 psi are even more preferred, as such pressures typically allow structures with sizes greater than 250 microns to be formed with some degree of dimensional control. Pressures less than 100 psi, which are referred to herein as "near-zero pressures," are most preferred, because at such pressures few limits exist on the size of internal and external cavities and channels that can be formed in the multilayered structure.

The pressure is preferably applied in the lamination process by means of a uniaxial press. Alternatively, pressures less than about 100 psi may be applied by hand.

As with semiconductor device fabrication, many devices may be present on each sheet. Accordingly, after lamination the multilayered structure may be diced using conventional green-sheet dicing or sawing apparatus to separate the individual devices. The high level of peel and shear resistance provided by the room-temperature adhesive results in the occurrence of very little edge delamination during the dicing process. If some layers become separated around the edges after dicing, the layers may be easily re-laminated by applying pressure to the affected edges by hand, without adversely affecting the rest of the device.

The final processing step is firing to convert the laminated multilayered green-sheet structure from its "green" state to form the finished, substantially monolithic, multilayered structure. The firing process occurs in two important stages as the temperature is raised. The first important stage is the binder burnout stage that occurs in the temperature range of about 250 to 50° C., during which the other organic materials, such as the binder in the green-sheet layers and the organic components in any applied thick-film pastes, are removed from the structure.

In the next important stage, the sintering stage, which occurs at a higher temperature, the inorganic particles sinter together so that the multilayered structure is densified and becomes substantially monolithic. The sintering temperature used depends on the nature of the inorganic particles present in the green-sheet. For many types of ceramics, appropriate sintering temperatures range from about 950 to about 1600° C., depending on the material. For example, for green-sheet containing aluminum oxide, sintering temperatures between 1400 and 1600° C. are typical. Other ceramic materials, such as silicon nitride, aluminum nitride, and silicon. carbide, require higher sintering temperatures, namely 1700 to 2200° C. For green-sheet with glass-ceramic particles, a sintering temperature in the range of 750 to 950° C. is typical. Glass particles generally require sintering temperatures in the range of only about 350 to 700° C. Finally, metal particles may require sintering temperatures anywhere from 550 to 1700° C., depending on the metal.

Typically, the devices are fired for a period of about 4 hours to about 12 hours or more, depending on the material used. Generally, the firing should be of a sufficient duration so as to remove the organic materials from the structure and to completely sinter the inorganic particles. In particular, polymers are present as a binder in the green-sheet and in the room-temperature adhesive. The firing should be of sufficient temperature and duration to decompose these polymers and to allow for their removal from the multilayered structure.

Typically, the multilayered structure undergoes a reduction in volume during the firing process. During the binder burnout phase, a small volume reduction of about 0.5 to 1.5% is normally observed. At higher temperatures, during the sintering stage, a further volume reduction of about 14 to 17% is typically observed.

As noted above, preferably any dissimilar materials added to the green-sheet layers are co-fired with them. Such dissimilar materials could be added as thick-film pastes or as other green-sheet layers. The benefit of co-firing is that the added materials are sintered to the green-sheet layers and become integral to the substantially monolithic microfluidic device. However, to be co-fireable, the added materials should have sintering temperatures and volume changes due to firing that are matched with those of the green-sheet layers. Sintering temperatures are largely material-dependent, so that matching sintering temperatures simply requires proper selection of materials. For example, although silver is the preferred metal for providing electrically conductive pathways, if the green-sheet layers contain alumina particles, which require a sintering temperature in the range of 1400 to 1600° C., some other metal, such as platinum, must be used due to the relatively low melting point of silver (961° C.).

The volume change due to firing, on the other hand, can be controlled. In particular, to match volume changes in two materials, such as green-sheet and thick-film paste, one should match: (1) the particle sizes; and (2) the percentage of organic components, such as binders, which are removed during the firing process. Additionally, volume changes need not be matched exactly, but any mismatch will typically result in internal stresses in the device. But symmetrical processing, placing the identical material or structure on opposite sides of the device can, to some extent, compensate for shrinkage mismatched materials. Too great a mismatch in either sintering temperatures or volume changes may result in defects in or failure of some or all of the device. For example, the device may separate into its individual layers, or it may become warped or distorted.

Figure 2:
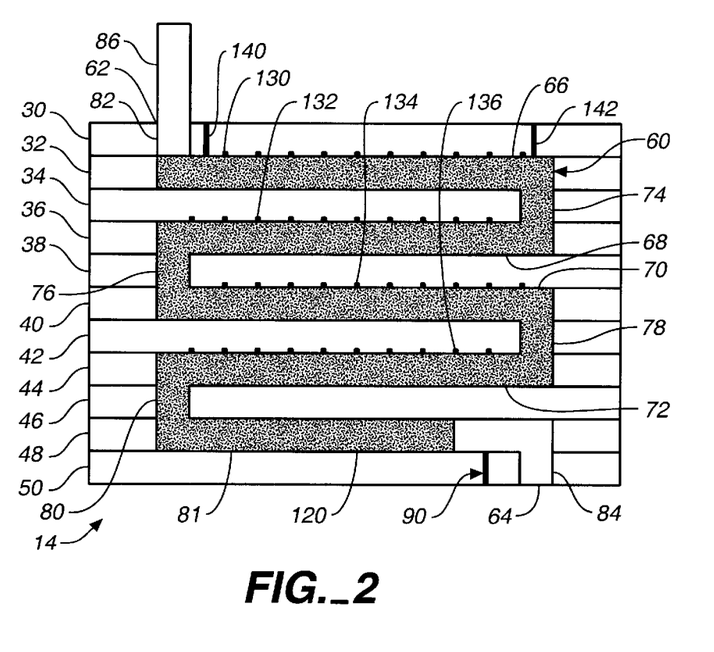
FIG. 2 is a sectional schematic view of a micro-gas chromatograph device, in accordance with a preferred embodiment of the present invention.

Shown in FIG. 2 is a cross-sectional view of a representative micro-gas chromatograph device 14. Device 10 is made from green-sheet layers 30–50 that have been laminated and sintered together to form a substantially monolithic structure, as described above. Device 14 includes a micro-gas chromatograph column 60 formed into layers 30–50. Column 60 extends from an inlet port 62 to an outlet port 64 and is preferably defined by a plurality of planar column sections connected in series by vias. For example, column 60 in FIG. 2 includes planar column sections 66–72 formed into layers 32, 36, 40, and 44, respectively. Vias 74, 76, and 78, formed into layers 34, 38, and 42, respectively, connect section 66 to section 68, section 68 to section 70, and section 70 to section 72, respectively. Although device 14 is shown in FIG. 2 with four planar column sections 66–72 for purposes of illustration, device 14 may include a greater or fewer number of planar column sections. Column 60 also includes an exit channel 81, formed into layer 48, that is connected to planar column section 72 by a via 80, formed into layer 46. Finally, a via 82, formed in layer 30, connects planar section 66 to inlet port 62, and a via 84, formed in layer 50 connects exit channel 81 to outlet 64. A gas inlet tube 86 is attached to gas chromatograph device 14 at inlet port 62, preferably by means of a high temperature adhesive. Gas inlet tube 86 connects device 14 with sample injection valve 18.

A detector 90, formed in layer 50, is preferably provided to detect the separated components as they travel along exit channel 81. Detector 90 is most conveniently provided as a thermal conductivity detector. One advantage of using a thermal conductivity detector is that it does not affect the sample. Thus, the sample exiting device 14 through outlet port 64 may be collected by another device for further analysis.

Figure 2A:
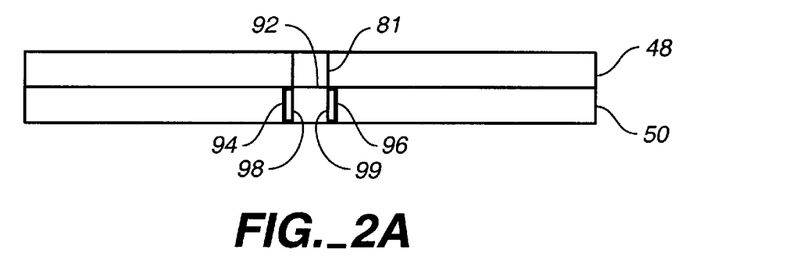
FIG. 2A is a sectional schematic view of the detector in the micro-gas chromatograph device of FIG. 2, in accordance with a preferred embodiment of the present invention.

As shown in FIG. 2A, thermal conductivity detector 90 comprises a resistor 92 disposed in exit channel 81 on the surface of layer 50. Current leads 94 and 96 are formed into layer 50 and connected to resistor 92, as shown in FIG. 2A, to allow a fixed current to be applied to resistor 92 from an external device, such as data processing system 26. Voltage leads 98 and 99 are also formed into layer 50 and connected to resistor 92, as shown in FIG. 2A to allow an external device, such as data processing system 26 to measure the voltage developed across resistor 92. Thermal conductivity detector 90 detects changes in the chemical composition of the gas passing through exit channel 81 as changes in the thermal conductivity of the gas, which, in turn, is detected as changes in the resistance of resistor 92. Resistor 92 is preferably made of a conductor with a high temperature coefficient, such as nickel. Resistor 92 is preferably formed by screen-printing a thick-film paste containing a conductor, such as nickel, onto green-sheet layer 50. In this way, resistor 92 will be sintered to layer 50 in the finished device. Similarly, leads 94, 96, 98, and 99 are preferably provided as conductor-filled vias sintered into layer 50.

Although detector 90 is preferably provided a thermal conductivity detector, detector 90 may also be a flame ionization or other detector used for gas chromatograph devices. Alternatively, the detector may be external to device 14, connected to outlet port 64.

Figure 3:
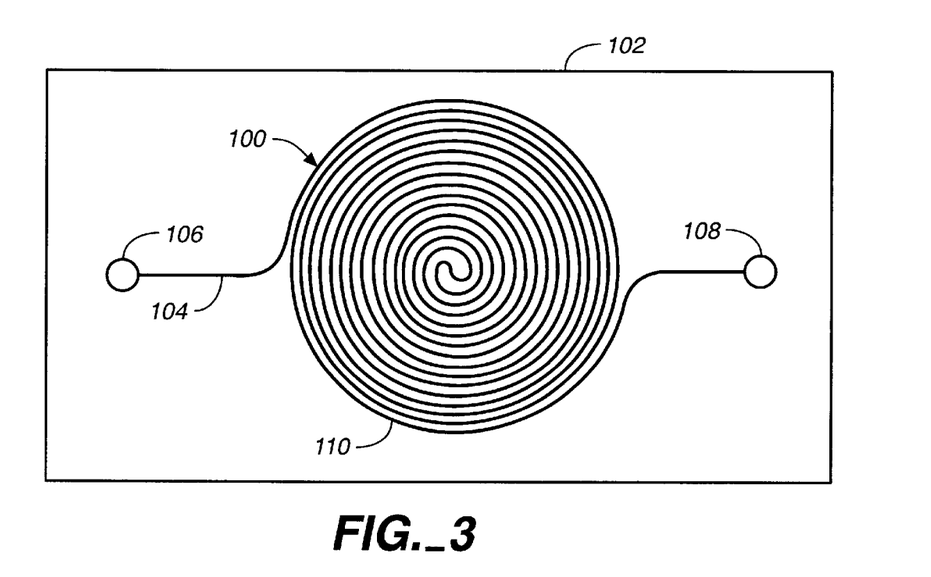
FIG. 3 is a top schematic view of a green-sheet layer with a planar column section defined therein, in accordance with a preferred embodiment of the present invention.

Each of planar column sections 66–72 comprises a channel formed into a green-sheet layer in a predetermined pattern. Preferably, the channel is defined by a pattern that efficiently fills up the area available in a given layer, in order to maximize the length of the channel. A particularly preferred pattern is an interlocking spiral, as shown in FIG. 3, however other patterns could also be used. With reference to FIG. 3, a representative planar column section 100 is formed into a layer 102. Section 100 is defined by a channel 104 extending from an input port 106 to an output port 108. Channel 104 is preferably 10–40 microns wide, 80–250 microns deep, and 0.1 to 1.0 meters long. Channel 104 may be formed by any of the techniques described herein for texturing green-sheet layers, such as embossing or punching. Accordingly, channel 104 may take up all of the thickness or only part of the thickness of green-sheet layer 102. Most of the length of channel is defined by an interlocking spiral pattern 110. The analyte gas, containing the sample gas and the carrier gas, enters section 100 through input port 106. The gas flows through channel 104 into spiral 110, where it is directed in a spiral path toward the center and then back to the edge of spiral 110. The gas then exits section 100 through output port 108.

Input port 106 and output port 108 are typically connected through vias formed in the layer above and the layer below layer 102 so as to interconnect section 100 with other portions of the gas-chromatograph column formed in other layer. For example, section 100 in FIG. 3 may correspond to planar column section 70 of device 14, shown in FIG. 2, in which case input port 106 would be connected to via 76 and output port 108 would be connected to via 78. In this way, multiple planar column sections may be interconnected in series to provide the desired length and, thus, separation efficiency, of the micro-gas chromatograph column.

Preferably, column 60 is filled with a porous ceramic plug 120 along most of its length. For example, in device 14 shown in FIG. 2, planar sections 66–72, vias 74–80, and part of exit channel 81 are filled with porous ceramic plug 120. Typically, detector 90 is located in apart of exit channel 81 not filled with porous ceramic plug 120, as shown in FIG. 2. Although ceramic plug 120 is shown in FIG. 2 as one continuous length for purposes of illustration, it may alternatively be made up of discrete lengths. For example, ceramic plug 120 may fill only planar column sections 66–72, instead. Porous ceramic plug 120 is preferably made of alumina or glass, with pore sizes of about 10 to 40 microns. Porous plug 120 is preferably formed by applying a thick-film paste, as described above, to the channels formed into the green-sheet layers defining column 60. In this way, plug 120 will become sintered into device 14 with the desired porosity.

Column 60 is also filled with a stationary phase for adsorbing the chemical components of the sample, as described above. Typical materials that can be used for the stationary phase include phenyl-methyl polysiloxane. In conventional gas chromatograph columns, the stationary phase simply-coats the walls of the column. However, with the provision of ceramic plug 120 into column 60, the stationary phase coats the pores in plug 120, thereby beneficially increasing the surface area of the stationary phase available to adsorb the chemical components. Accordingly, the addition of porous ceramic plug 120 increases the separation efficiency of column 60 for a given length.

Planar column sections 66–72 may also be provided with heaters 130–136, respectively. In this way, each column section 66–72 may be heated to a different temperature so as to effect better separation in column 60. Heaters 130–136 may be provided in various configurations, though, in a particularly convenient configuration shown in FIG. 2, heaters 130–136 are formed on the lower surface of layers 30, 34, 38, and 42, respectively, adjacent to the corresponding one of column sections 66–72 formed into the layer below. In this way, each heater 130–136 is in good thermal contact with its corresponding column section 66–72. However, layers 34, 38, and 42 separate each one of heaters 132–136 from the other column sections so as to provide thermal isolation between column sections 66–72. In particular, the ceramic materials that typically make up layers 30–50 have a low thermal conductivity.

Figure 2B:
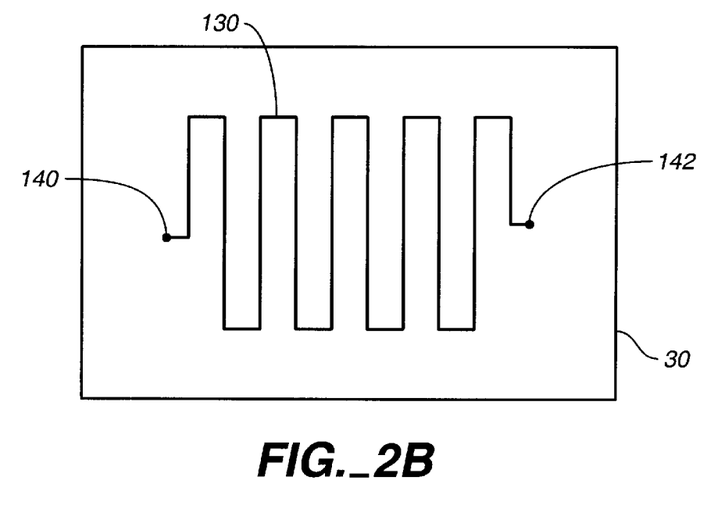
FIG. 2B is a top schematic view of one of the. layers of the micro-gas chromatograph device of FIG. 2, in accordance with a preferred embodiment of the present invention.

FIG. 2B, which is an axial view of the lower surface of layer 30, i.e., the interface with layer 32, shows heater 130 in greater detail. Heater 130 comprises a serpentine trace 130 extending between a first lead 140 and second lead 142. Trace 130 is preferably made by depositing, such as by screen printing, conductive material in the form of a thick-film paste onto the surface of layer 30. Leads 140 and 142 are formed into layer 30 as conductor-filled vias. The structure of heaters 132–136 is similar.

Although various embodiments of this invention have been shown and described, it should be understood that various modifications and substitutions, as well as rearrangements and combinations of the preceding embodiments, can be made by those skilled in the art, without departing from the novel spirit and scope of this invention.

We claim:

1. A method for making a multilayered micro-gas chromatograph device, said method comprising the steps of:

texturing a plurality of green-sheet layers in a predetermined pattern, said green-sheet layers including particles selected from the group consisting of ceramic particles, glass particles, and glass-ceramic particles, said predetermined pattern defining a micro-gas chromatograph column;

applying a first thick-film paste to at least a first predetermined portion of said predetermined pattern in said green-sheet layers; and sintering said green-sheet layers together at a predetermined temperature for a predetermined amount of time to form a substantially monolithic structure, said substantially monolithic structure having said micro-gas chromatograph column defined therein and a porous plug disposed in said micro-gas chromatograph column, wherein at least part of said porous plug is defined by said first predetermined portion.

2. A method for making a multilayered micro-gas chromatograph device, said method comprising the steps of:

texturing a plurality of green-sheet layers in a predetermined pattern, said green-sheet layers including particles selected from the group consisting of ceramic particles, glass particles, and glass-ceramic particles, said predetermined pattern defining a micro-gas chromatograph column;

applying a first thick-film paste to at least a portion of said predetermined pattern in said green-sheet layers; and sintering said green-sheet layers together at a predetermined temperature for a predetermined amount of time to form a substantially monolithic structure, said substantially monolithic structure having said micro-gas chromatograph column defined therein and a porous plug disposed in said micro-gas chromatograph column;

wherein said micro-gas chromatograph column includes an exit channel, further comprising the step of applying a second thick-film paste to a surface of one of said green-sheet layers to define a resistor disposed in said exit channel.

3. The method of claim 1 or 2, wherein said first thick film paste contains particles selected from the group consisting of alumina particles and glass particles.

4. The method of claim 1 or 2, further comprising the step of adding a stationary phase to said micro-gas chromatograph column so that at least a portion of said stationary phase is disposed in the pores of said porous plug.

5. The method of claim 1 or 2, wherein said micro-gas chromatograph column includes a plurality of planar column sections, each one of said planar column sections being defined by a channel formed into one of said green-sheet layers.

6. The method of claim 5 or 2, further comprising the step of applying a third thick-film paste to a surface of one of said green-sheet layers to define a heater, said heater being disposed for raising the temperature of one of said planar column sections with respect to the other planar column sections.

7. The method of claim 1, further comprising applying a first thick-film paste to a second predetermined portion of said predetermined pattern in said green-sheet layers; and wherein said porous plug comprises two discrete portions, a first defined by said first predetermined portion, and a second defined by said second predetermined portion.

* * * * *

UNITED STATES PATENT AND TRADEMARK OFFICE
CERTIFICATE OF CORRECTION

| | | |
|---|---|---|
| PATENT NO. | : 6,527,890 B1 | Page 1 of 1 |
| APPLICATION NO. | : 09/460283 | |
| DATED | : March 4, 2003 | |
| INVENTOR(S) | : Cynthia Briscoe et al. | |

It is certified that error appears in the above-identified patent and that said Letters Patent is hereby corrected as shown below:

In claim 7, column 12, line 7, after "The method of claim 1" insert --or claim 2--.

Signed and Sealed this

Thirty-first Day of March, 2009

JOHN DOLL
*Acting Director of the United States Patent and Trademark Office*